(12) United States Patent
Clavijo et al.

(10) Patent No.: US 12,059,536 B2
(45) Date of Patent: Aug. 13, 2024

(54) STABILIZATION DEVICE, SYSTEM, AND METHODS THEREOF FOR INTEGRATED CATHETERS

(71) Applicant: Becton, Dickinson and Company, Franklin Lakes, NJ (US)

(72) Inventors: Cristian Clavijo, Orem, UT (US); Jon K. Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 570 days.

(21) Appl. No.: 16/777,714

(22) Filed: Jan. 30, 2020

(65) Prior Publication Data
US 2020/0246592 A1    Aug. 6, 2020

Related U.S. Application Data

(60) Provisional application No. 62/800,324, filed on Feb. 1, 2019.

(51) Int. Cl.
*A61M 25/02*    (2006.01)
*A61M 25/00*    (2006.01)

(52) U.S. Cl.
CPC ........ *A61M 25/02* (2013.01); *A61M 25/0097* (2013.01); *A61M 2025/0246* (2013.01);
(Continued)

(58) Field of Classification Search
CPC .............. A61M 25/02; A61M 25/0097; A61M 2205/0205; A61M 2025/0266;
(Continued)

(56) References Cited

U.S. PATENT DOCUMENTS

| | | |
|---|---|---|
| 2,525,398 A | 10/1950 | Collins |
| 2,553,961 A | 12/1950 | Rousseau et al. |

(Continued)

FOREIGN PATENT DOCUMENTS

| | | |
|---|---|---|
| CA | 995995 A1 | 8/1976 |
| CA | 2228747 A1 | 2/1997 |

(Continued)

OTHER PUBLICATIONS

Plaintiff's Opening Claim Construction Brief; *Venetec International Inc.* v. *Nexus Medical, LLC*, U.S. District Court for Delaware, Case No. 07-CV-0057***, Oct. 10, 2008.

(Continued)

*Primary Examiner* — Lauren P Farrar
(74) *Attorney, Agent, or Firm* — Rutan & Tucker LLP

(57) ABSTRACT

Disclosed is a stabilization device and system for stabilizing integrated catheters, and associated methods. The stabilization device can include a platform and a dressing. The platform can have a skin-adhering side configured to stick to a patient's skin and catheter-securing side configured to secure an integrated catheter. The catheter-securing side of the platform can include a contoured recess extending into a body of the platform configured to secure a catheter tube or a hub of the integrated catheter, as well as an extension port of the integrated catheter, a wing assembly of the integrated catheter, or both the extension port and the wing assembly. The dressing can include a transparent polymeric film over a textile pad. The dressing can have a skin-adhering side configured to adhere the dressing to both the integrated catheter secured in the platform and the patient's skin.

16 Claims, 8 Drawing Sheets

(52) U.S. Cl.
CPC ............... *A61M 2025/0266* (2013.01); *A61M 2205/0205* (2013.01)

(58) Field of Classification Search
CPC .... A61M 2025/0246; A61M 2025/028; A61M 25/0637
See application file for complete search history.

(56) References Cited

U.S. PATENT DOCUMENTS

| | | |
|---|---|---|
| 2,707,953 A | 5/1955 | Ryan |
| 2,893,671 A | 7/1959 | Flora et al. |
| 3,046,984 A | 7/1962 | Eby |
| 3,059,645 A | 10/1962 | Hasbrouck et al. |
| 3,064,648 A | 11/1962 | Bujan |
| 3,167,072 A | 1/1965 | Stone et al. |
| 3,204,636 A | 9/1965 | Kariher et al. |
| 3,256,880 A | 6/1966 | Caypinar |
| 3,289,671 A | 12/1966 | Troutman et al. |
| 3,471,109 A | 10/1969 | Meyer |
| 3,482,569 A | 12/1969 | Raaelli, Sr. |
| 3,524,443 A | 8/1970 | Batlin |
| 3,526,880 A | 9/1970 | Caypinar |
| 3,529,597 A | 9/1970 | Fuzak |
| 3,542,321 A | 11/1970 | Kahabka |
| 3,556,096 A | 1/1971 | Fuller et al. |
| 3,602,227 A | 8/1971 | Andrew |
| 3,630,195 A | 12/1971 | Santomieri |
| 3,632,071 A | 1/1972 | Cameron et al. |
| 3,677,250 A | 7/1972 | Thomas |
| 3,700,574 A | 10/1972 | Kehr |
| 3,731,684 A | 5/1973 | Spiegel |
| 3,766,915 A | 10/1973 | Rychlik |
| 3,834,380 A | 9/1974 | Boyd |
| 3,847,370 A | 11/1974 | Engelsher |
| 3,856,020 A | 12/1974 | Kovac |
| 3,896,527 A | 7/1975 | Miller et al. |
| 3,900,026 A | 8/1975 | Wagner |
| 3,906,946 A | 9/1975 | Nordstrom |
| 3,942,228 A | 3/1976 | Buckman et al. |
| 3,942,750 A | 3/1976 | Noorily |
| 3,973,565 A | 8/1976 | Steer |
| 3,973,656 A | 8/1976 | Zumbro |
| 3,993,081 A | 11/1976 | Cussell |
| 4,020,835 A | 5/1977 | Nordstrom et al. |
| 4,030,540 A | 6/1977 | Roma |
| 4,057,066 A | 11/1977 | Taylor |
| 4,059,105 A | 11/1977 | Cutruzzula et al. |
| 4,082,094 A | 4/1978 | Dailey |
| 4,114,618 A | 9/1978 | Vargas |
| 4,114,626 A | 9/1978 | Beran |
| 4,129,128 A | 12/1978 | McFarlane |
| 4,133,307 A | 1/1979 | Ness |
| 4,142,527 A | 3/1979 | Garcia |
| 4,149,539 A | 4/1979 | Cianci |
| 4,161,177 A | 7/1979 | Fuchs |
| 4,170,995 A | 10/1979 | Levine et al. |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,353,369 A | 10/1982 | Muetterties et al. |
| 4,356,599 A | 11/1982 | Larson et al. |
| 4,362,156 A | 12/1982 | Feller, Jr. et al. |
| 4,389,754 A | 6/1983 | Sohma |
| 4,392,853 A | 7/1983 | Muto |
| 4,392,857 A | 7/1983 | Beran |
| 4,397,647 A | 8/1983 | Gordon |
| 4,405,163 A | 9/1983 | Voges et al. |
| 4,442,994 A | 4/1984 | Logsdon |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,484,913 A | 11/1984 | Swauger |
| 4,490,141 A | 12/1984 | Lacko et al. |
| 4,498,903 A | 2/1985 | Mathew |
| 4,500,338 A | 2/1985 | Young et al. |
| 4,502,477 A | 3/1985 | Lewis |
| 4,516,293 A | 5/1985 | Beran |
| 4,516,968 A | 5/1985 | Marshall et al. |
| 4,517,971 A | 5/1985 | Sorbonne |
| 4,533,349 A | 8/1985 | Bark |
| 4,534,762 A | 8/1985 | Heyer |
| 4,563,177 A | 1/1986 | Kamen |
| 4,579,120 A | 4/1986 | MacGregor |
| 4,583,976 A | 4/1986 | Ferguson |
| 4,589,702 A | 5/1986 | Bach et al. |
| 4,617,017 A | 10/1986 | Hubbard et al. |
| 4,621,029 A | 11/1986 | Kawaguchi |
| 4,623,102 A | 11/1986 | Hough, Jr. |
| 4,633,863 A | 1/1987 | Filips et al. |
| 4,636,552 A | 1/1987 | Gay et al. |
| 4,650,473 A | 3/1987 | Bartholomew et al. |
| 4,659,329 A | 4/1987 | Annis |
| 4,660,555 A | 4/1987 | Payton |
| 4,661,110 A | 4/1987 | Fortier et al. |
| 4,669,156 A | 6/1987 | Guido et al. |
| 4,699,616 A | 10/1987 | Nowak et al. |
| 4,711,636 A | 12/1987 | Bierman |
| D293,717 S | 1/1988 | Proulx et al. |
| 4,726,716 A | 2/1988 | McGuire |
| 4,733,666 A | 3/1988 | Mercer, Jr. |
| 4,737,143 A | 4/1988 | Russell |
| 4,742,824 A | 5/1988 | Payton et al. |
| 4,762,513 A | 8/1988 | Choy et al. |
| 4,775,121 A | 10/1988 | Carty |
| 4,808,162 A | 2/1989 | Oliver |
| 4,823,789 A | 4/1989 | Beisang, III |
| 4,826,486 A | 5/1989 | Palsrok et al. |
| 4,828,549 A | 5/1989 | Kvalo |
| 4,838,878 A | 6/1989 | Kalt et al. |
| 4,852,844 A | 8/1989 | Villaveces |
| 4,857,058 A | 8/1989 | Payton |
| 4,863,432 A | 9/1989 | Kvalo |
| 4,869,465 A | 9/1989 | Yirmiyahu et al. |
| 4,874,380 A | 10/1989 | Hesketh |
| 4,880,412 A | 11/1989 | Weiss |
| 4,881,705 A | 11/1989 | Kraus |
| 4,896,465 A | 1/1990 | Rhodes et al. |
| 4,897,082 A | 1/1990 | Erskine |
| 4,898,587 A | 2/1990 | Mera |
| 4,899,963 A | 2/1990 | Murphy |
| 4,919,654 A | 4/1990 | Kalt |
| D308,576 S | 6/1990 | Iversen |
| 4,932,943 A | 6/1990 | Nowak |
| 4,944,728 A | 7/1990 | Carrell et al. |
| 4,952,207 A | 8/1990 | Lemieux |
| 4,955,864 A | 9/1990 | Hajduch |
| 4,976,700 A | 12/1990 | Tollini |
| 4,997,421 A | 3/1991 | Palsrok et al. |
| 5,000,741 A | 3/1991 | Kalt |
| 5,037,397 A | 8/1991 | Kalt et al. |
| 5,073,166 A | 12/1991 | Parks et al. |
| 5,073,170 A | 12/1991 | Schneider |
| 5,078,731 A | 1/1992 | Hayhurst |
| 5,084,026 A | 1/1992 | Shapiro |
| 5,098,399 A | 3/1992 | Tollini |
| 5,112,313 A | 5/1992 | Sallee |
| 5,147,322 A | 9/1992 | Bowen et al. |
| 5,156,641 A | 10/1992 | White |
| 5,163,914 A | 11/1992 | Abel |
| 5,188,609 A | 2/1993 | Bayless et al. |
| 5,192,273 A | 3/1993 | Bierman |
| 5,192,274 A | 3/1993 | Bierman |
| 5,195,981 A | 3/1993 | Johnson |
| 5,224,935 A | 7/1993 | Hollands |
| 5,226,892 A | 7/1993 | Boswell |
| 5,234,185 A | 8/1993 | Hoffman et al. |
| 5,250,041 A | 10/1993 | Folden et al. |
| 5,257,768 A | 11/1993 | Juenemann et al. |

(56) References Cited

U.S. PATENT DOCUMENTS

| | | |
|---|---|---|
| 5,263,939 A | 11/1993 | Wortrich |
| 5,263,943 A | 11/1993 | Vanderbrook |
| 5,266,401 A | 11/1993 | Tollini |
| 5,267,967 A | 12/1993 | Schneider |
| 5,280,866 A | 1/1994 | Ueki |
| 5,282,463 A | 2/1994 | Hammersley |
| 5,290,248 A | 3/1994 | Bierman et al. |
| 5,292,312 A | 3/1994 | Delk et al. |
| 5,304,146 A | 4/1994 | Johnson et al. |
| 5,306,243 A | 4/1994 | Bonaldo |
| D347,060 S | 5/1994 | Bierman |
| 5,308,337 A | 5/1994 | Bingisser |
| 5,314,411 A | 5/1994 | Bierman et al. |
| 5,318,546 A | 6/1994 | Bierman |
| 5,322,514 A | 6/1994 | Steube et al. |
| 5,330,438 A | 7/1994 | Gollobin et al. |
| 5,334,186 A | 8/1994 | Alexander |
| 5,336,195 A | 8/1994 | Daneshvar |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,345,931 A | 9/1994 | Battaglia, Jr. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,368,575 A | 11/1994 | Chang |
| 5,374,254 A | 12/1994 | Buma |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,389,082 A | 2/1995 | Baugues et al. |
| 5,395,344 A | 3/1995 | Beisang, III et al. |
| 5,397,639 A | 3/1995 | Tollini |
| 5,398,679 A | 3/1995 | Freed |
| 5,403,285 A | 4/1995 | Roberts |
| 5,413,562 A | 5/1995 | Swauger |
| 5,443,460 A | 8/1995 | Miklusek |
| 5,449,349 A | 9/1995 | Sallee et al. |
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |
| 5,474,572 A | 12/1995 | Hayhurst |
| 5,484,420 A | 1/1996 | Russo |
| 5,494,245 A | 2/1996 | Suzuki et al. |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,522,803 A | 6/1996 | Teissen-Simony |
| 5,527,293 A | 6/1996 | Zamierowski |
| 5,539,020 A | 7/1996 | Bracken et al. |
| 5,549,567 A | 8/1996 | Wolman |
| 5,551,421 A | 9/1996 | Noureldin et al. |
| D375,355 S | 11/1996 | Bierman |
| D375,356 S | 11/1996 | Bierman |
| 5,578,013 A | 11/1996 | Bierman |
| D377,831 S | 2/1997 | Bierman |
| 5,613,655 A | 3/1997 | Marion |
| 5,616,135 A | 4/1997 | Thorne et al. |
| 5,626,565 A | 5/1997 | Landis et al. |
| 5,632,274 A | 5/1997 | Quedens et al. |
| 5,637,098 A | 6/1997 | Bierman |
| 5,643,217 A | 7/1997 | Dobkin |
| 5,653,411 A | 8/1997 | Picco et al. |
| 5,672,159 A | 9/1997 | Warrick |
| 5,676,137 A | 10/1997 | Byrd |
| 5,681,290 A | 10/1997 | Alexander |
| 5,685,859 A | 11/1997 | Kornerup |
| 5,690,617 A | 11/1997 | Wright |
| 5,693,032 A | 12/1997 | Bierman |
| 5,697,907 A | 12/1997 | Gaba |
| 5,702,371 A | 12/1997 | Bierman |
| D389,911 S | 1/1998 | Bierman |
| 5,722,959 A | 3/1998 | Bierman |
| D393,903 S | 4/1998 | Bierman |
| 5,738,660 A | 4/1998 | Luther |
| 5,755,225 A | 5/1998 | Hutson |
| 5,776,106 A | 7/1998 | Matyas |
| 5,785,201 A | 7/1998 | Bordner et al. |
| 5,795,335 A | 8/1998 | Zinreich |
| 5,800,402 A | 9/1998 | Bierman |
| 5,810,781 A | 9/1998 | Bierman |
| D399,954 S | 10/1998 | Bierman |
| 5,827,230 A | 10/1998 | Bierman |
| 5,827,239 A | 10/1998 | Dillon et al. |
| D401,329 S | 11/1998 | Bierman |
| 5,833,663 A | 11/1998 | Bierman et al. |
| 5,846,255 A | 12/1998 | Casey |
| D404,815 S | 1/1999 | Bierman |
| 5,855,591 A | 1/1999 | Bierman |
| 5,916,199 A | 6/1999 | Miles |
| 5,921,991 A | 7/1999 | Whitehead et al. |
| 5,922,470 A | 7/1999 | Bracken et al. |
| 5,941,263 A | 8/1999 | Bierman |
| 5,944,696 A | 8/1999 | Bayless et al. |
| 6,001,081 A | 12/1999 | Collen |
| 6,015,119 A | 1/2000 | Starchevich |
| 6,024,761 A | 2/2000 | Barone et al. |
| 6,027,480 A | 2/2000 | Davis et al. |
| 6,054,523 A | 4/2000 | Braun et al. |
| D425,619 S | 5/2000 | Bierman |
| 6,074,368 A | 6/2000 | Wright |
| 6,113,577 A | 9/2000 | Hakky et al. |
| 6,117,163 A | 9/2000 | Bierman |
| 6,131,575 A | 10/2000 | Lenker et al. |
| 6,132,398 A | 10/2000 | Bierman |
| 6,132,399 A | 10/2000 | Shultz |
| 6,206,897 B1 | 3/2001 | Jamiolkowski et al. |
| 6,213,979 B1 | 4/2001 | Bierman |
| 6,224,571 B1 | 5/2001 | Bierman |
| 6,228,064 B1 | 5/2001 | Abita et al. |
| 6,231,548 B1 | 5/2001 | Bassett |
| 6,258,066 B1 | 7/2001 | Urich |
| 6,273,873 B1 | 8/2001 | Fleischer |
| 6,274,786 B1 | 8/2001 | Heller |
| 6,283,945 B1 | 9/2001 | Bierman |
| 6,290,676 B1 | 9/2001 | Bierman |
| 6,332,874 B1 | 12/2001 | Eliasen et al. |
| 6,361,523 B1 | 3/2002 | Bierman |
| 6,387,075 B1 | 5/2002 | Stivland et al. |
| 6,387,076 B1 | 5/2002 | Landuyt |
| 6,413,240 B1 | 7/2002 | Bierman et al. |
| 6,419,660 B1 | 7/2002 | Russo |
| 6,428,514 B1 | 8/2002 | Goebel et al. |
| 6,428,515 B1 | 8/2002 | Bierman et al. |
| 6,447,485 B2 | 9/2002 | Bierman |
| 6,458,104 B2 | 10/2002 | Gautsche |
| 6,491,664 B2 | 12/2002 | Bierman |
| 6,500,154 B1 | 12/2002 | Hakky et al. |
| D470,936 S | 2/2003 | Bierman |
| 6,551,285 B1 | 4/2003 | Bierman |
| 6,572,588 B1 | 6/2003 | Bierman et al. |
| 6,582,403 B1 | 6/2003 | Bierman et al. |
| 6,585,703 B1 | 7/2003 | Kassel et al. |
| 6,596,402 B2 | 7/2003 | Soerens et al. |
| D480,144 S | 9/2003 | Adams et al. |
| 6,663,600 B2 | 12/2003 | Bierman et al. |
| 6,685,670 B2 | 2/2004 | Miles et al. |
| 6,703,120 B1 | 3/2004 | Ko et al. |
| D492,411 S | 6/2004 | Bierman |
| 6,770,055 B2 | 8/2004 | Bierman et al. |
| 6,786,892 B2 | 9/2004 | Bierman |
| 6,796,310 B2 | 9/2004 | Bierman |
| 6,829,705 B2 | 12/2004 | Smith |
| 6,837,875 B1 | 1/2005 | Bierman |
| 6,872,194 B2 | 3/2005 | Doyle et al. |
| D503,977 S | 4/2005 | Bierman |

(56) References Cited

U.S. PATENT DOCUMENTS

| | | | |
|---|---|---|---|
| 6,951,550 B2 | 10/2005 | Bierman | |
| 6,984,145 B1 | 1/2006 | Lim | |
| 7,018,362 B2 | 3/2006 | Bierman et al. | |
| 7,074,208 B2 | 7/2006 | Pajunk et al. | |
| 7,115,321 B2 | 10/2006 | Soerens et al. | |
| 7,320,681 B2 | 1/2008 | Gillis et al. | |
| 7,354,421 B2 | 4/2008 | Bierman | |
| 7,879,013 B2 | 2/2011 | Smith et al. | |
| 8,052,648 B2 | 11/2011 | Dikeman et al. | |
| 8,394,067 B2 | 3/2013 | Bracken et al. | |
| 8,915,885 B2 | 12/2014 | Smith et al. | |
| 9,616,200 B2 | 4/2017 | Smith et al. | |
| 9,642,987 B2 | 5/2017 | Bierman et al. | |
| 10,322,262 B2 | 6/2019 | Bracken et al. | |
| 10,561,815 B2 | 2/2020 | Bierman et al. | |
| 2002/0026152 A1 | 2/2002 | Bierman | |
| 2002/0095119 A1 | 7/2002 | Bertoch et al. | |
| 2002/0161332 A1 | 10/2002 | Ramey | |
| 2002/0165493 A1 | 11/2002 | Bierman | |
| 2003/0125668 A1 | 7/2003 | Bierman | |
| 2004/0167475 A1 | 8/2004 | Wright et al. | |
| 2005/0137496 A1 | 6/2005 | Walsh et al. | |
| 2005/0192539 A1 | 9/2005 | Bierman et al. | |
| 2005/0205708 A1 | 9/2005 | Sasaki et al. | |
| 2005/0282977 A1 | 12/2005 | Stempel et al. | |
| 2006/0025723 A1 | 2/2006 | Ballarini | |
| 2006/0129103 A1 | 6/2006 | Bierman et al. | |
| 2006/0233652 A1 | 10/2006 | Kim et al. | |
| 2006/0289011 A1 | 12/2006 | Helsel | |
| 2007/0032561 A1 | 2/2007 | Lin et al. | |
| 2007/0142782 A2 | 6/2007 | Bierman | |
| 2007/0142784 A1 | 6/2007 | Dikeman et al. | |
| 2007/0265572 A1 | 11/2007 | Smith et al. | |
| 2007/0276335 A1 | 11/2007 | Bierman | |
| 2008/0029476 A1 | 2/2008 | Ohmi et al. | |
| 2008/0097334 A1 | 4/2008 | Dikeman et al. | |
| 2008/0249476 A1 | 10/2008 | Bierman et al. | |
| 2009/0137962 A1 | 5/2009 | Bracken et al. | |
| 2009/0149814 A1* | 6/2009 | Bailey | A61M 25/065 604/180 |
| 2010/0100049 A1 | 4/2010 | Godfrey | |
| 2010/0298778 A1 | 11/2010 | Bracken et al. | |
| 2011/0060295 A1* | 3/2011 | Hen | A61L 15/44 604/290 |
| 2013/0150827 A1 | 6/2013 | Bracken et al. | |
| 2015/0112270 A1 | 4/2015 | Smith et al. | |
| 2015/0217088 A1* | 8/2015 | Zyzelewski | A61B 46/23 128/852 |
| 2016/0193452 A1* | 7/2016 | Hanson | A61F 13/0253 602/52 |
| 2017/0216556 A1 | 8/2017 | Bierman et al. | |
| 2019/0247623 A1* | 8/2019 | Helm | A61F 13/0243 |
| 2019/0247625 A1 | 8/2019 | Bracken et al. | |
| 2020/0171273 A1 | 6/2020 | Bierman et al. | |

FOREIGN PATENT DOCUMENTS

| | | | |
|---|---|---|---|
| CA | 2208577 A1 | 5/1997 | |
| CA | 2306802 A1 | 4/1999 | |
| CA | 2310030 A1 | 5/1999 | |
| CA | 2281457 A1 | 2/2001 | |
| CA | 2402507 A1 | 9/2001 | |
| CA | 2418000 A1 | 2/2002 | |
| CA | 2483995 A1 | 4/2004 | |
| DE | 2341297 A1 | 4/1975 | |
| DE | 3110023 A1 | 9/1982 | |
| DE | 8811131 U1 | 1/1989 | |
| DE | 4000380 A1 | 8/1990 | |
| DE | 29608294 U1 | 8/1996 | |
| EP | 0064284 A2 | 11/1982 | |
| EP | 0247590 A2 | 12/1987 | |
| EP | 0274418 A2 | 7/1988 | |
| EP | 0356683 A1 | 3/1990 | |
| EP | 0440101 A2 | 8/1991 | |
| EP | 0470709 A1 | 2/1992 | |
| EP | 0597213 A1 | 5/1994 | |
| EP | 0931560 A1 | 7/1999 | |
| FR | 1184139 A | 7/1959 | |
| FR | 2381529 A1 | 9/1978 | |
| FR | 2722414 A1 | 1/1996 | |
| FR | 2852520 A1 | 9/2004 | |
| GB | 2063679 A | 6/1981 | |
| GB | 2086466 A | 5/1982 | |
| GB | 2219034 A | 11/1989 | |
| GB | 2233902 A | 1/1991 | |
| GB | 2288542 A | 10/1995 | |
| GB | 2312619 A | 11/1997 | |
| JP | 52-004691 B | 2/1977 | |
| JP | S60-051377 | 4/1985 | |
| JP | 63501477 | 6/1988 | |
| JP | 01308572 | 12/1989 | |
| JP | 1992-051767 | 3/1992 | |
| JP | H04-037448 | 3/1992 | |
| JP | 06-063153 | 3/1994 | |
| JP | 1995-028563 | 5/1995 | |
| JP | 08024344 | 1/1996 | |
| JP | H08-257138 A | 10/1996 | |
| NL | 1015663 C2 | 1/2002 | |
| WO | 8001458 A1 | 7/1980 | |
| WO | 8502774 A1 | 7/1985 | |
| WO | 86/06641 A1 | 11/1986 | |
| WO | 9116939 A1 | 11/1991 | |
| WO | 9219309 A1 | 11/1992 | |
| WO | 9610435 A1 | 4/1996 | |
| WO | 9626756 A1 | 9/1996 | |
| WO | 9853872 A1 | 12/1998 | |
| WO | WO-2015035238 A1 * | 3/2015 | A61M 25/02 |
| WO | 2018/138324 A1 | 8/2018 | |

OTHER PUBLICATIONS

Plantiff's Answering Brief in Opposition to Defendant's Motion for Summary Judgement of invalidity; Filed: Oct. 30, 2008; *Venetec International Inc. v. Nexus Medical, LLC*; USDC, District of Delaware, Civil Action No. 07-cv-0057-MPT. (Oct. 30, 2008).

Rebuttal Expert Report of Dr. Terry N. Layton, Ph.D., *Venetec International Inc. v. Nexus Medical, LLC*, U.S. District Court for Delaware, Case No. 07-CV-0057***, Aug. 29, 2008, 33 pgs.

Request for Inter Partes Reexamination Under 37 C.F.R. 1.913 [filed Jun. 25, 2007]. In re Bierman, USPTO, Reexamination No. 95/000,271.

Search Result, Percufix® Catheter Cuff Kit, downloaded from the Internet on Aug. 15, 2001.

Second Supplemental Complaint [filed Sep. 5, 2007]. *Venetec Int'l, Inc. v. Nexus Medical, LLC*, USDC D.Del., Case No. 1:07-CV-00057.

Stipulation and Order amending Nexus Medical, LLC's Answer to Complaint and Counterclaim, *Venetec International Inc. v. Nexus Medical, LLC*, U.S. District Court for Delaware, Case No. 07-CV-005, 15 pgs. (Jul. 13, 2007).

Third-Party Requester's Response to Patent Owner's Response to Office Action Dated Sep. 21, 2007, Inter Partes Reexamination No. 95/000,271, filed Dec. 21, 2007, 85 pages.

Third-Party Requester's Supplemental Response to Patent Owner's Supplemental Response to Office Action Dated Sep. 21, 2007, Inter Partes Reexamination No. 95/000,271, filed Jan. 22, 2008, 48 pgs.

Transcript of Claim Construction Hearing; *Venetec International Inc. v. Nexus Medical, LLC*, U.S. District Court for Delaware, Case No. 07-CV-0057***, Nov. 21, 2008.

Tri-State Hospital Supply Corporation, Centurion Healthcare Products brochure for HubGuard Catheter Securement (Mar. 3, 2004).

Tri-State Hospital Supply Corporation, Centurion Healthcare Products brochure for IV Start Kits (Sep. 14, 2004).

Tri-State Hospital Supply Corporation, Centurion Healthcare Products brochure for LineGuard J-Loop Securement Device (Nov. 2, 2004).

Tri-State Hospital Supply Corporation, Centurion Healthcare Products brochure for Port Access Trays (Apr. 24, 2003).

Tri-State Hospital Supply Corporation, Centurion Healthcare Products brochure for SorbaView 2000 Window Dressing (Apr. 14, 2004).

(56) References Cited

OTHER PUBLICATIONS

Tri-State Hospital Supply Corporation, Centurion Healthcare Products brochure for SorbaView Ultimate Window Dressing (May 7, 2004 and Jun. 22, 2004).
U.S. Appl. No. 12/063,225, filed Feb. 7, 2008 Final Office Action dated Jun. 21, 2016.
U.S. Appl. No. 12/063,225, filed Feb. 7, 2008 Non-Final Office Action dated Nov. 30, 2015.
U.S. Appl. No. 12/063,225, filed Feb. 7, 2008 Notice of Allowance dated Jan. 6, 2017.
U.S. Appl. No. 13/762,803, filed Feb. 8, 2013 Board Decision dated Jul. 3, 2018.
U.S. Appl. No. 13/762,803, filed Feb. 8, 2013 Non-Final Office Action dated Jul. 2, 2015.
U.S. Appl. No. 13/762,803, filed Feb. 8, 2013 Notice of Allowance dated Oct. 10, 2018.
U.S. Appl. No. 13/762,803, filed Feb. 8, 2013 Examiner's Answer dated Dec. 1, 2016.
U.S. Appl. No. 13/762,803, filed Feb. 8, 2013 Final Office Action dated Oct. 30, 2015.
U.S. Appl. No. 14/580,720, filed Dec. 23, 2014 Non-Final Office Action dated Sep. 9, 2016.
U.S. Appl. No. 15/489,594, filed Apr. 17, 2017 Advisory Action dated Jun. 12, 2019.
U.S. Appl. No. 15/489,594, filed Apr. 17, 2017 Final Office Action dated Mar. 7, 2019.
U.S. Appl. No. 15/489,594, filed Apr. 17, 2017 Non-Final Office Action dated Sep. 28, 2018.
U.S. Appl. No. 15/489,594, filed Apr. 17, 2017 Notice of Allowance dated Oct. 1, 2019.
U.S. Appl. No. 90/010,167 filed May 15, 2008 Decision by the Board of Patent Appeals and Interferences (BPSI) in the Ex Parte Reexamination of the '949 patent, dated Aug. 24, 2010.
U.S. Appl. No. 90/010,211, filed Jun. 27, 2008 Decision by the Board of Patent Appeals and Interferences (BPAI) in the Ex Parte Reexamination of the '150 patent, dated Sep. 7, 2010.
Venetec International, Inc.'s Reply to Nexus Medical, LLC's Counterclaim [filed Apr. 11, 2007]. *Venetec Int'l, Inc. v. Nexus Medical, LLC*, USDC D.Del., Case No. 1:07-CV-00057.
Venetec International, Inc.'s Reply to Nexus Medical, LLC's Counterclaim [filed Aug. 28, 2007]. *Venetec Int'l, Inc. v. Nexus Medical, LLC*, USDC D.Del., Case No. 1:07-CV-00057.
Venetec International, Inc.'s Reply to Nexus Medical, LLC's Counterclaim [filed Sep. 27, 2007]. *Venetec Int'l, Inc. v. Nexus Medical, LLC*, USDC D.Del., Case No. 1:07-CV-00057.
Venetec's letter to Judge Thynge dated Sep. 28, 2007, *Venetec International Inc. v. Nexus Medical, LLC*, U.S. District Court for Delaware, Case No. 07-CV-0057***, 6 pgs.
Venetec's Motion for Partial Judgement on the Pleadings, *Venetec International Inc. v. Nexus Medical, LLC*, U.S. District Court for Delaware, Case No. 07-CV-0057, 3 pgs. (Sep. 28, 2007).
Venetec's Motion for Partial Judgement on the Pleadings, *Venetec International Inc. v. Nexus Medical, LLC*, U.S. District Court for Delaware, Case No. 07-CV-0057, 34 pgs. (Sep. 28, 2007).
Venetec's Opening Brief in Support of Motion for Partial Judgement on the Pleadings, *Venetec International Inc. v. Nexus Medical, LLC*, U.S. District Court for Delaware, Case No. 07-Cv-0057, 34 pgs. (Sep. 28, 2007).
Zefon International printout from www.zefon.com/medical/griplok.htm depicting prior art GRIP-LOK Universal Tubing Securement Device (printed Jun. 20, 2005).
"Occlude". Merriam-Webster Online Dictionary. <http://www.merriam-webster.com/dictionary/occlude>. Last accessed May 12, 2011.
3M Technical Data Sheet entitled "Adhesive Transfer Tapes with Adhesive 300MP 9692-9695-964" (Sep. 2002).
Bostick Findley Product Data Sheet entitled "4229 Hot Melt Adhesives" (Sep. 2003).
Brief in Support of Nexus Medical, LLC's Motion for Summary Judgement of Noninfringement of the Venetec Patents (Public Redacted Version); *Venetec International Inc. v. Nexus Medical, LLC*, U.S. District Court for Delaware, Case No. 07-CV-0057, Public version filed Oct. 24, 2008, 158 pgs.
Brief in Support of Nexus Medical, LLC's Motion for Summary Judgement that the Venetec Patents are Invalid; *Venetec International Inc. v. Nexus Medical, LLC*, USDC, District of Delaware, Civil Action No. 07-cv-0057-MPT. Dated Oct. 10, 2008.
CA 2,619,979 filed Aug. 31, 2006 Office Action dated Oct. 7, 2015.
Civil Docket for Case No. 1:07-CV-00057*** [printed Oct. 22, 2007].
Complaint [dated Jan. 29, 2007]. *Venetec Int'l, Inc. v. Nexus Medical, LLC*, USDC D.Del., Case No. 1:07-CV-00057.
Declaration of Jennifer C. Bailey in Support of Nexus' Opposition to Venetec's Motion for Partial Judgement on the Pleadings, *Venetec International Inc. v. Nexus Medical, LLC*, U.S. District Court for Delaware, Case No. 07-CV-0057, 31 pgs. (Mar. 15, 2007).
Defendant Nexus Medical, LLC's Objections and Responses to Plantiff Venetec International, Inc's Modified and Supplemental Definitions Set Forth in its First Set of interrogatories to Defendant Nexus Medical, LLC, *Venetec International Inc. v. NexusMedical, LLC*, U.S. District Court for Delaware, Case No. 07-Cv-0057, 79 pgs. (May 30, 2007).
Defendant Nexus Medical, LLC's Reply to Plantiff's Answering Brief in Opposition to Defendant's Motion for Summary Judgement of Invalidity; Filed: Nov. 10, 2008; *Venetec International Inc. v. Nexus Medical, LLC*; USDC, District of Delaware, CivilAction No. 07-cv-0057-MPT. (Nov. 10, 2008).
Defendant Nexus Medical, LLC's Reply to Plantiff's Answering Brief in Opposition to Defendant's Motion for Summary Judgement of Noninfringement of the Venetec Patents (Public Version); *Venetec International Inc. v. Nexus Medical, LLC*, U.S. DistrictCourt for Delaware, Case No. 07-CV-0057, Public version filed Nov. 18, 2008, 27 pgs.
EP 04 07 6329 European Search Report dated Feb. 7, 2005.
EP 06 802789 (PCT/US2006/034203) Supplementary Partial European Search Report dated May 15, 2009.
Expert Report of Julie E. Shomo Regarding Invalidity of the Venetec Patents Pursuant to Rule 26(a)(2)(B), *Venetec International Inc. v. Nexus Medical, LLC*, U.S. District Court for Delaware, Case No. 07-CV-0057***, Jul. 18, 2008, 31pgs.
Expert Report of Marvin Gordon Regarding Invalidity of the Venetec Patents Pursuant to Rule 26(a)(2)(B), *Venetec International Inc. v. Nexus Medical, LLC*, U.S. District Court for Delaware, Case No. 07-CV-0057***, Jul. 18, 2008, 23 pgs.
Expert Report of William H. Hirsch Regarding Invalidity of the Venetec Patents Pursuant to Rule 26(a)(2)(B), *Venetec International Inc. v. Nexus Medical, LLC*, U.S. District Court for Delaware. Case No. 07-CV-0057, Jul. 18. 2008, 39 pgs.
First Supplemental Complaint [dated Jul. 24, 2007]. *Venetec Int'l, Inc. v. Nexus Medical, LLC*, USDC D.Del., Case No. 1:07-CV-00057.
Hi-Tech Products Material Data Sheet entitled "Tricot PSA" (printed prior to Jul. 13, 2006).
Interview Summary in the Ex Parte Reexamination of the '150 patent, U.S. Appl. No. 90/010,211, mailed Dec. 19, 2008, 3 pgs.
Interview Summary in the Ex Parte Reexamination of the '979 patent, U.S. Appl. No. 90/010,167, mailed Dec. 19, 2008, 4 pgs.
Joint Claim Construction Chart; *Venetec International Inc. v. Nexus Medical, LLC*, U.S. District Court for Delaware, Case No. 07-CV-0057***, Oct. 10, 2008, 91 pgs.
Judge Thynge's Order Denying Nexus Motion to Stay Proceedings Pending Reexamination, *Venetec International Inc. v. Nexus Medical, LLC*, U.S. District Court for Delaware, Case No. 07-CV 0057***, 1 pg. (Oct. 12, 2007).
Memorandum Order; *Venetec International Inc. v. Nexus Medical, LLC*, U.S. District Court for Delaware, Case No. 07-CV-0057***, Mar. 28, 2008, 16 pgs.
Nexus Medical, LLC's First Amended Answer and Counterclaim to Venetec International, Inc.'s Second Supplemental Complaint and Counterclaim; *Venetec International Inc. v. Nexus Medical, LLC*, U.S. District Court for Delaware, Case No. 07-CV-0057, 50pgs. (Mar. 10, 2008).

(56) References Cited

OTHER PUBLICATIONS

Nexus Medical LLC's Opening Claim Construction Brief; *Venetec International Inc. v. Nexus Medical, LLC*, U.S. District Court for Delaware, Case No. 07-CV-0057***, Oct. 10, 2008.

Nexus Medical, LLC's Answer to Venetec International, Inc.'s Complaint and Counterclaim [dated Mar. 22, 2007]. *Venetec Int'l, Inc. v. Nexus Medical, LLC*, USDC D.Del., Case No. 1:07-CV-00057.

Nexus Medical, LLC's Answer to Venetec International, Inc.'s First Supplemental Complaint and Counterclaim [dated Aug. 8, 2007]. *Venetec Int'l, Inc. v. Nexus Medical, LLC*, USDC D.Del., Case No. 1:07-CV-00057.

Nexus Medical, LLC's Answer to Venetec International, Inc.'s Second Supplemental Complaint and Counterclaim [filed Sep. 19, 2007]. *Venetec Int'l, Inc. v. Nexus Medical, LLC*, USDC D.Del., Case No. 1:07-CV-00057.

Nexus Medical, LLC's Objections and Responses to Venetec International, Inc's First Set of Interrogatories, *Venetec International Inc. v. Nexus Medical, LLC*, U.S. District Court for Delaware Case No. 07-CV-0057***. (Aug. 27, 2007).

Nexus' letter to Judge Thynge dated Sep. 27, 2007, *Venetec International Inc. v. Nexus Medical, LLC*, U.S. District Court for Delaware, Case No. 07-CV-0057***.

Nexus' Opposition to Venetec's Motion for Partial Judgement on the Pleadings, *Venetec International Inc. v. Nexus Medical, LLC*, U.S. District Court for Delaware, Case No. 07-CV-0057, 28 pgs. (Oct. 15, 2007).

Notice of Assignment of Inter Partes Reexamination Request for the '485 patent, *Venetec International Inc. v. Nexus Medical, LLC*, U,S. District Court for Delaware, Case No. 07-CV-0057 1 pg. (Jul. 10, 2007).

Notice of Assignment of Reexamination, U.S. Appl. No. 90/010,211, mailed Jul. 7, 2008, 1 pg.

Notice of Reexamination Request Filing Date, U.S. Appl. No. 90/010,211, mailed Jul. 7, 2008, 1 pg.

Office Action in the Ex Parte Reexamination of the '150 patent, U.S. Appl. No. 90/010,211, dated May 11, 2009.

Office Action in the Ex Parte Reexamination of the '979 patent, U.S. Appl. No. 90/010,167, dated May 8, 2009.

Office Action issued to Venetec in the Ex Parte Reexamination of the '150 patent, U.S. Appl. No. 90/010,211, mailed Nov. 7, 2008, 20 pgs.

Office Action issued to Venetec in the Ex Parte Reexamination of the '979 patent, U.S. Appl. No. 90/010,167, mailed Nov. 7, 2008, 21 pgs.

Office Action issued to Venetec in the Inter Partes Reexamination, *Venetec International Inc. v. Nexus Medical, LLC*, U.S. District Court for Delaware, Case No. 07-CV-0057***, 23 pgs. (Sep. 21, 2007).

Order Granting Inter Partes Reexamination, *Venetec International Inc. v. Nexus Medical, LLC*, U.S. District Court for Delaware, Case No. 07-CV-0057***. Sep. 21, 2007.

Order Granting Request for Ex Parte Reexamination of the '150 patent, U.S. Appl. No. 90/010,211, mailed Jul. 29, 2008, 16 pgs.

Order Granting Request for Ex Partes Reexamination, Ex Parte Reexamination of the '979 patent, U.S. Appl. No. 90/010,167, filed Jul. 29, 2008, 14 pgs.

Order Granting Request for Inter Partes Reexamination & Reexamination Non-Final Office Action, Inter Partes Reexamination No. U.S. Appl. No. 95/000,271, filed Sep. 21, 2007,50 pgs.

Patent Owner's Response to Office Action issued to Venetec in the Ex Parte Reexamination of the '150 patent, U.S. Appl. No. 90/010,211, filed Jan. 7, 2009, 36 pgs.

Patent Owner's Response to Office Action issued to Venetec in the Ex Parte Reexamination of the '979 patent, U.S. Appl. No. 90/010,167, Jan. 7, 2009.

Patent Owner's Response to Office Action, Inter Partes Reexamination No. 95/000,271, filed Nov. 21, 2007, 90 pgs.

Patent Owner's Supplemental Response to Office Action, Inter Partes Reexamination No. 95/000,271, filed Sep. 29, 2008, 46 pgs.

Patent Owner's Supplemental Response to Office Action, Inter Partes Reexamination No. 95/000,271, filed Dec. 21, 2007, 46 pgs.

PCT/US06/34203 filed Aug. 31, 2006 International Search Report dated Aug. 7, 2007.

U.S. Appl. No. 16/394,969, filed Apr. 25 2019 Non-Final Office Action dated Aug. 3, 2021.

EP 20747735.7 filed Aug. 18, 2021, Extended European Search Report dated Sep. 6, 2022.

U.S. Appl. No. 16/394,969, filed Apr. 25 2019 Non-Final Office Action dated Jun. 14, 2022.

U.S. Appl. No. 16/783,009, filed Feb. 5, 2020, Non-Final Office Action dated Aug. 4, 2022.

\* cited by examiner

STABILIZATION DEVICE, SYSTEM, AND METHODS THEREOF FOR INTEGRATED CATHETERS

PRIORITY

This application claims the benefit of priority to U.S. Provisional Application No. 62/800,324, filed Feb. 1, 2019, which is incorporated by reference in its entirety into this application.

BACKGROUND

A peripheral intravenous catheter ("PIVC") often needs to be prematurely removed from a patient before an intended IV therapy is complete. A primary factor contributing to the need to prematurely remove a PIVC is mechanical phlebitis, which results when the PIVC moves around and irritates the internal anatomy of the patient. Mechanical stabilization of PIVCs has been shown to decrease mechanical phlebitis and increase IV-therapy dwell time. However, existing stabilization devices for such PIVCs are not compatible with integrated PIVCs. Thus, the existing stabilization devices cannot provide the mechanical stabilization needed to reduce mechanical phlebitis and enhance the dwell time needed to complete intended IV therapies with integrated PIVCs. Disclosed herein is a stabilization device and methods thereof for integrated catheters such as integrated PIVCs.

SUMMARY

Disclosed herein is a stabilization system for integrated catheters including, in some embodiments, a platform and a dressing. The platform has a skin-adhering side and catheter-securing side. The catheter-securing side of the platform includes a contoured recess extending into a body of the platform configured to secure a hub of an integrated catheter having an extension port, a wing assembly, or both the extension port and the wing assembly. The dressing is configured to cover the platform together with the integrated catheter secured in the platform over a patient's skin.

In some embodiments, the body of the platform is a foam-like material, the skin-adhering side of the platform has a first adhesive thereon configured to adhere to the patient's skin, and the catheter-securing side of the platform has a second adhesive thereon configured to adhere to the integrated catheter.

In some embodiments, the skin-adhering side and the catheter-securing side of the platform are parallel to each other from a catheter tube-securing front-end portion of the platform to an opposite, back-end portion of the platform.

In some embodiments, the skin-adhering side and the catheter-securing side of the platform are oblique to each other from a catheter tube-securing front-end portion of the platform to an opposite, back-end portion of the platform.

In some embodiments, the front-end portion of the platform includes a cutout extending through the skin-adhering side of the platform configured for accessing a percutaneous insertion site.

In some embodiments, the stabilization system further includes an antimicrobial pad configured for placement around the insertion site, a topical medicament including an antimicrobial agent configured for application around the insertion site, or a skin adhesive configured for sealing the insertion site. The antimicrobial pad is optionally integrated into the body on the skin-adhering side of the platform. The skin adhesive optionally includes a same or different antimicrobial agent than the topical medicament.

In some embodiments, the contoured recess is symmetrical for securing the extension port of the integrated catheter on either a starboard side of the platform or an opposite, port side of the platform.

In some embodiments, the dressing includes a transparent polymeric film over a textile pad. The textile pad has a cutout configured to form a window for viewing a distal end of a catheter tube of the integrated catheter when the dressing covers the platform together with the integrated catheter secured in the platform over the patient's skin.

In some embodiments, the dressing includes a skin-adhering side configured to adhere the dressing to both the integrated catheter secured in the platform and the patient's skin.

In some embodiments, the dressing includes a through hole or slit in at least a starboard side of the dressing or an opposite, port-side of the dressing configured for the extension port or an extension tube of the integrated catheter to pass therethrough.

Also disclosed herein is a stabilization system for integrated catheters including, in some embodiments, a platform and a dressing. The platform has a skin-adhering side configured to stick to a patient's skin and catheter-securing side configured to secure an integrated catheter. The catheter-securing side of the platform includes a contoured recess extending into a body of the platform configured to secure a catheter tube or a hub of the integrated catheter, as well as an extension port of the integrated catheter, a wing assembly of the integrated catheter, or both the extension port and the wing assembly. The dressing includes a transparent polymeric film over a textile pad. The dressing has a skin-adhering side configured to adhere the dressing to both the integrated catheter secured in the platform and the patient's skin.

In some embodiments, the body of the platform is a foam-like material and the contoured recess is symmetrical for securing the extension port of the integrated catheter on either a starboard side of the platform or an opposite, port side of the platform.

In some embodiments, the skin-adhering side and the catheter-securing side of the platform are oblique to each other from a catheter tube-securing front-end portion of the platform to an opposite, back-end portion of the platform.

In some embodiments, the textile pad has a cutout configured to form a window for viewing a distal end of the catheter tube of the integrated catheter when the dressing covers the platform together with the integrated catheter secured in the platform over the patient's skin.

In some embodiments, the dressing includes a through hole or slit in at least a starboard side of the dressing or an opposite, port-side of the dressing configured for the extension port or an extension tube of the integrated catheter to pass therethrough.

In some embodiments, the stabilization system further includes an antimicrobial pad configured for placement around the insertion site, a topical medicament including an antimicrobial agent configured for application around the insertion site, or a skin adhesive configured for sealing the insertion site. The antimicrobial pad is optionally integrated into the body on the skin-adhering side of the platform. The skin adhesive optionally includes a same or different antimicrobial agent than the topical medicament.

Also disclosed herein is a method for stabilizing integrated catheters including, in some embodiments, removing a first adhesive backing from a catheter-securing side of a platform of a stabilization device to expose a contoured recess extending into a body of the platform; securing an integrated catheter in the contoured recess by adhering it thereto, the integrated catheter including a catheter tube, a hub, and an extension port, a wing assembly, or both the extension port and the wing assembly; removing a second adhesive backing from a skin-adhering side of the platform; adhering the platform to a stabilization site on a patient's skin near a percutaneous insertion site; removing a third adhesive backing from a skin-adhering side of a dressing of the stabilization device; and adhering the dressing to the integrated catheter, the platform, and the patient's skin, thereby stabilizing the integrated catheter and decreasing risk of mechanical phlebitis.

In some embodiments, the method further includes viewing a distal end of the catheter tube at the insertion site through a window of the dressing formed by a transparent polymeric film over a cutout in a textile pad.

In some embodiments, the method further includes inserting the extension port or an extension tube of the integrated catheter through a through hole or slit in at least a starboard side of the dressing or an opposite, port-side of the dressing configured and taping the extension tube about the stabilization site to further secure the integrated catheter.

In some embodiments, the method further includes degreasing the patient's skin at the stabilization site with a degreasing wipe before adhering the platform to the patient's skin.

These and other features of the concepts provided herein will become more apparent to those of skill in the art in view of the accompanying drawings and following description, which disclose particular embodiments of such concepts in greater detail.

DRAWINGS

DESCRIPTION

Figure 1:
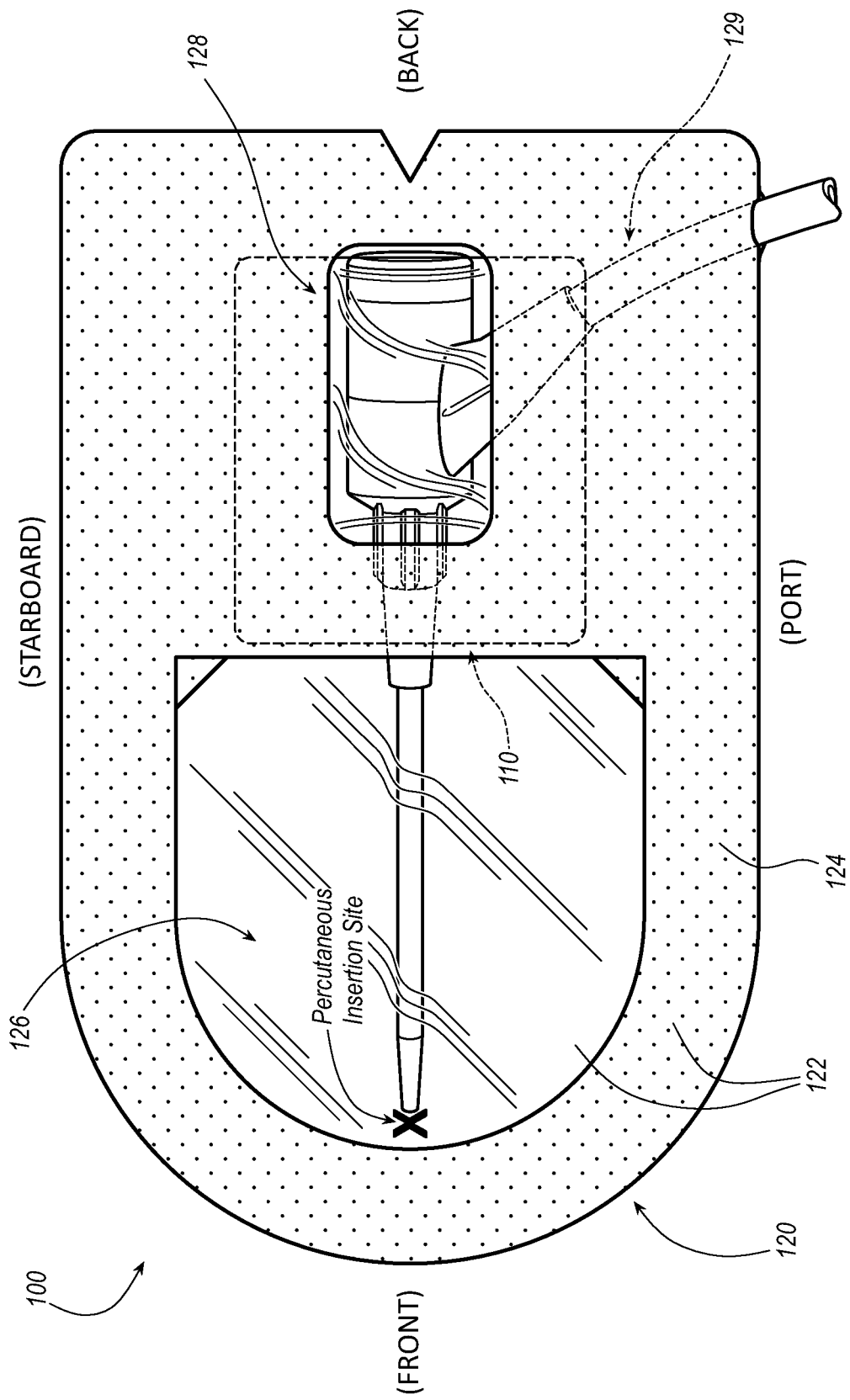
FIG. 1 illustrates a stabilization device for integrated catheters stabilizing an integrated catheter at a stabilization site of a patient adjacent a percutaneous insertion site in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

With respect to terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "integrated catheter," an integrated catheter is a one-piece manufacturer-assembled device including a catheter tube fluidly connected to at least one extension tube by way of a hub therebetween. An integrated catheter is different than a non-integrated catheter, which must be assembled by a clinician or the like prior to use.

With respect to "proximal," as in a "proximal portion" or a "proximal end portion" of, for example, a catheter disclosed herein, "proximal" refers to a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," as in a "distal portion" or a "distal end portion" of, for example, a catheter disclosed herein, "distal" refers to a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

With respect to "stabilization site," a stabilization site is the site at which an integrated catheter is to be stabilized or already stabilized on a patient.

Unless defined otherwise, all technical and scientific terms used herein have the same meaning as commonly understood by those of ordinary skill in the art.

A peripheral intravenous catheter ("PIVC") often needs to be prematurely removed from a patient before an intended IV therapy is complete. A primary factor contributing to the need to prematurely remove a PIVC is mechanical phlebitis, which results when the PIVC moves around and irritates the internal anatomy of the patient. Mechanical stabilization of PIVCs has been shown to decrease mechanical phlebitis and increase IV-therapy dwell time. However, existing stabilization devices for such PIVCs are not compatible with integrated PIVCs. Thus, the existing stabilization devices cannot provide the mechanical stabilization needed to reduce mechanical phlebitis and enhance the dwell time needed to complete intended IV therapies with integrated PIVCs. Disclosed herein is a stabilization device and methods thereof for integrated catheters such as integrated PIVCs.

FIG. 1 illustrates a stabilization device 100 for integrated catheters stabilizing an integrated catheter at a stabilization site of a patient including a percutaneous insertion site in accordance with some embodiments.

As shown, the stabilization device 100 includes a platform 110 and a dressing 120. For expository expediency, a front or front-end portion of the stabilization device 100 is intended to be placed at or about the insertion site. A back or back-end portion of the stabilization device 100 is opposite the front or front-end portion of the stabilization device 100. The back or back-end portion of the stabilization device 100 is intended to be placed distal to the insertion site. Borrowing from nautical or aeronautical terms for orientation, a starboard side of the stabilization device 100 is the right-hand side of the stabilization device 100 as if standing on the stabilization device 100 and looking toward the front or front-end portion of the stabilization device 100. A port side of the stabilization device 100 is opposite the starboard side of the stabilization device 100. The port side of the stabilization device 100 is the left-hand side of the stabilization device 100 as if standing on the stabilization device 100 and looking toward the front or front-end portion of the stabilization device 100. Such terms are used herein with respect to the platform 110 and the dressing 120 as well.

Figure 2A:
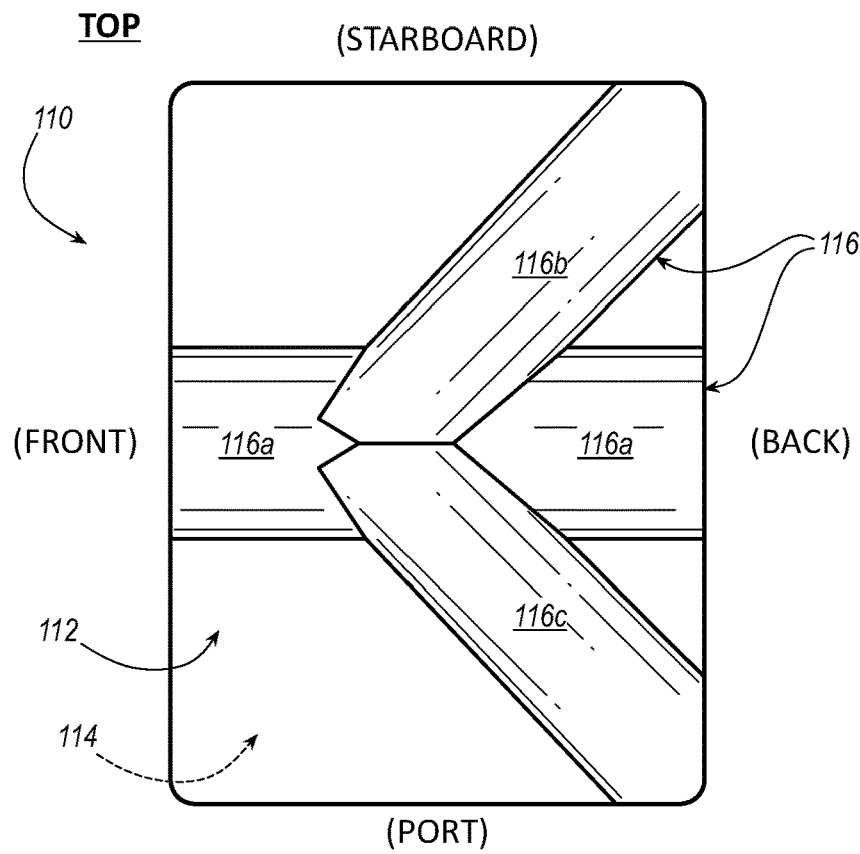
FIG. 2A illustrates a view of a top of a platform of the stabilization device in accordance with some embodiments.
Figure 2B:
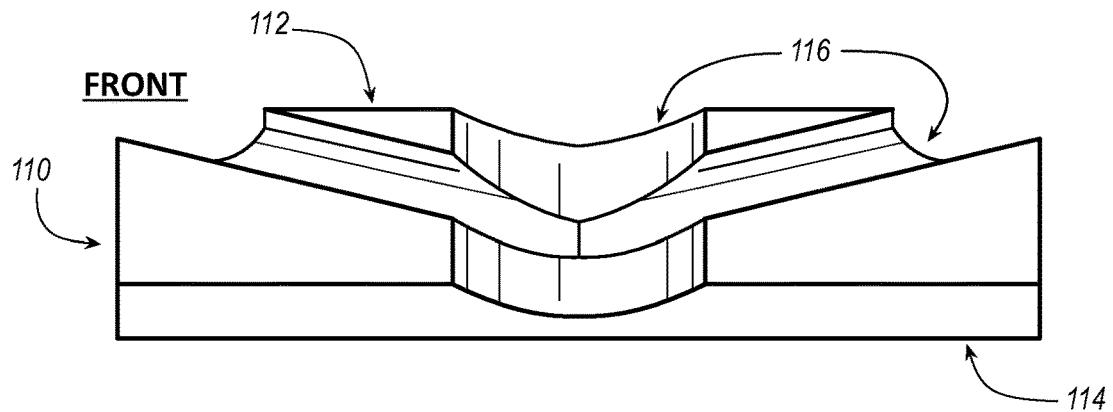
FIG. 2B illustrates a view of a front of the platform of the stabilization device in accordance with some embodiments.
Figure 2C:
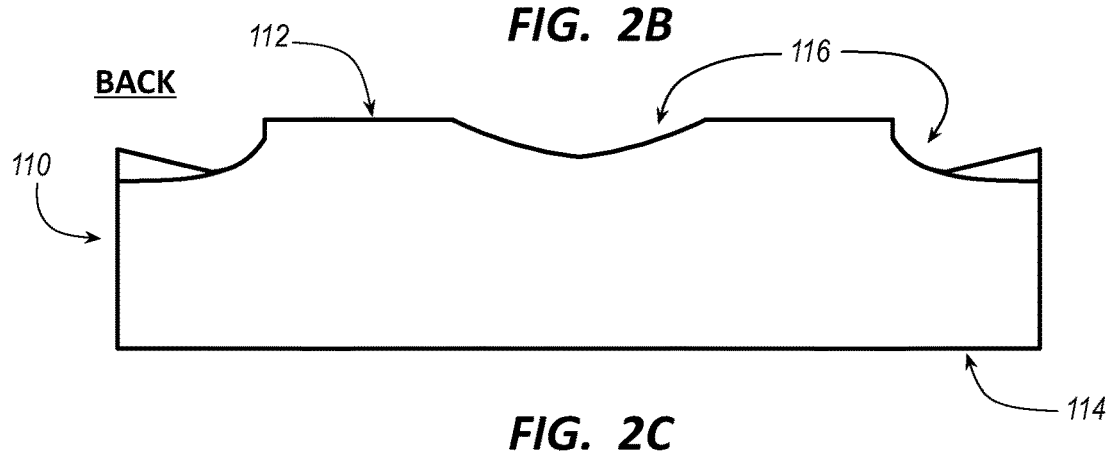
FIG. 2C illustrates a view of a back of the platform of the stabilization device in accordance with some embodiments.
Figure 3A:
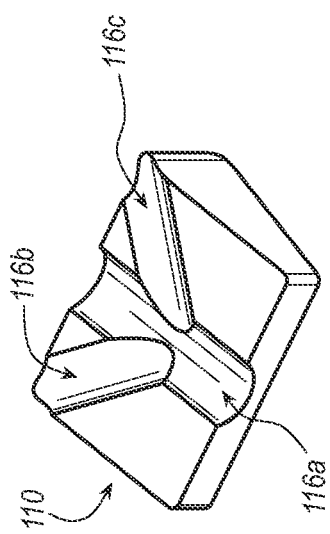
FIG. 3A illustrates the platform of the stabilization device without an integrated catheter in accordance with some embodiments.

FIGS. 2A, 2B, and 2C respectively illustrate a view from above the platform 110 of the stabilization device 100, a view from the front of the platform 110 of the stabilization device, and a view from the back of the platform 110 of the stabilization device 100 in accordance with some embodiments. FIG. 3A also illustrates an oblique view of the platform 110 of the stabilization device 100 without an integrated catheter in accordance with some embodiments.

As shown, the platform 110 has a skin-adhering side 114 and a catheter-securing side 112. The skin-adhering side 114 of the platform 110 has a first adhesive thereon configured to adhere to a patient's skin, while the catheter-securing side 112 of the platform 110 has a second adhesive thereon configured to adhere to an integrated catheter. The first and second adhesives can be the same or different.

Figure 3B:
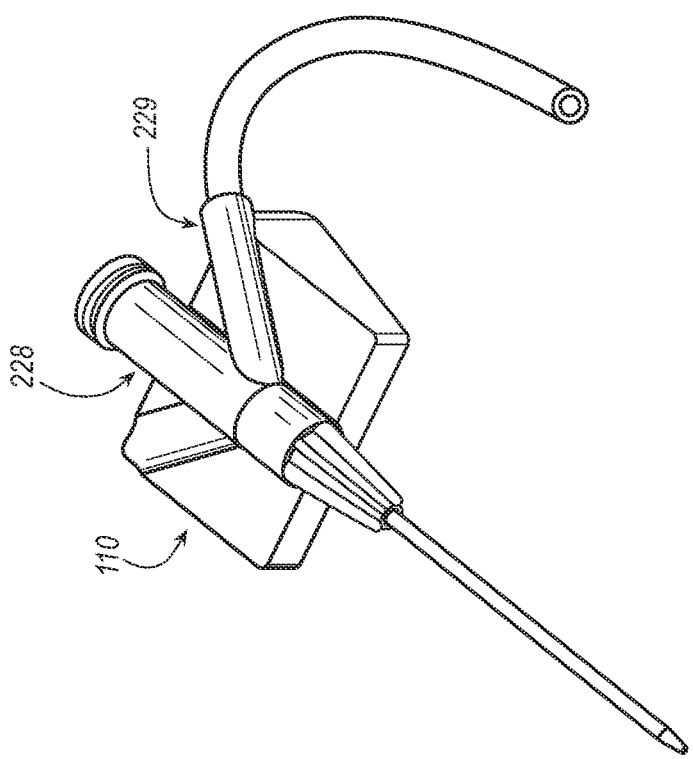
FIG. 3B illustrates the platform of the stabilization device with an integrated catheter in accordance with some embodiments.
Figure 3C:
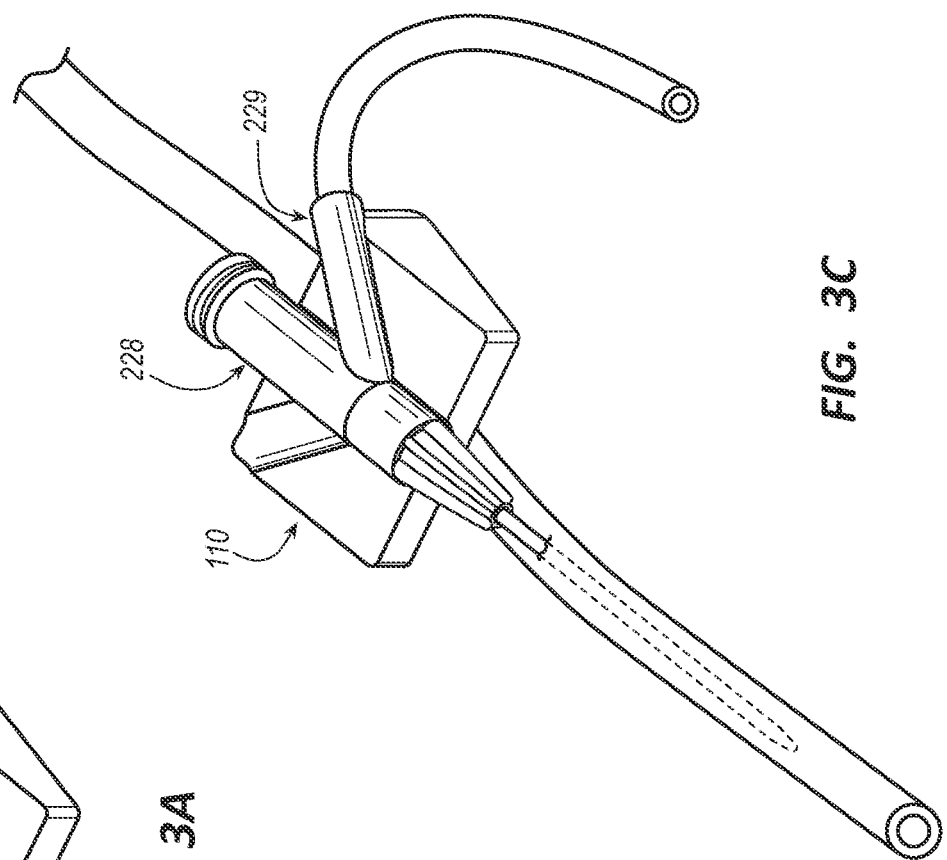
FIG. 3C illustrates the platform of the stabilization device with an integrated catheter inserted into a model vein in accordance with some embodiments.

The catheter-securing side 112 of the platform 110 includes a contoured recess 116 extending into a medically suitable foam-like body of the platform 110, the foam-like body being adaptable to a curved surface such as a patient's hand or arm. The contoured recess 116 is configured to secure a catheter tube or a hub of the integrated catheter having an extension port angled with respect to the hub, a wing assembly, or both the extension port and the wing assembly. For example, a contoured-recess portion 116a is configured to secure the catheter tube or the hub 228 of an integrated catheter, while each portion of the contoured-recess portions 116b and 116c is configured to secure the extension port 229 of an integrated catheter or an extension tube extending therefrom. See FIGS. 3A, 3B, and 3C, which illustrate the platform 110 of the stabilization device 100 with an integrated catheter secured in the contoured recess 116 of the platform 110, the latter figure with the integrated catheter inserted into a model vein.

Figure 4B:
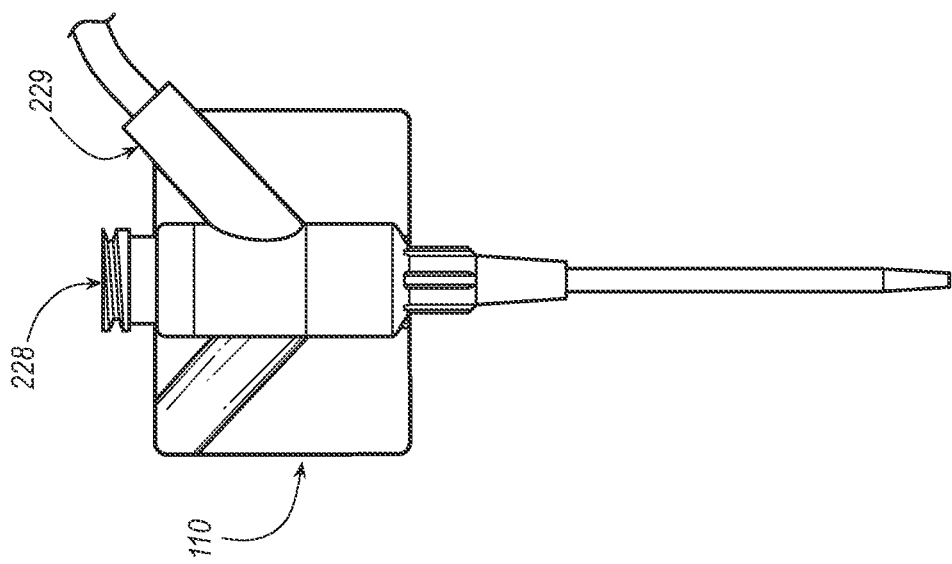
FIG. 4B illustrates the platform of the stabilization device with the extension port of the integrated catheter in a port-side recess of the platform in accordance with some embodiments.
Figure 4A:
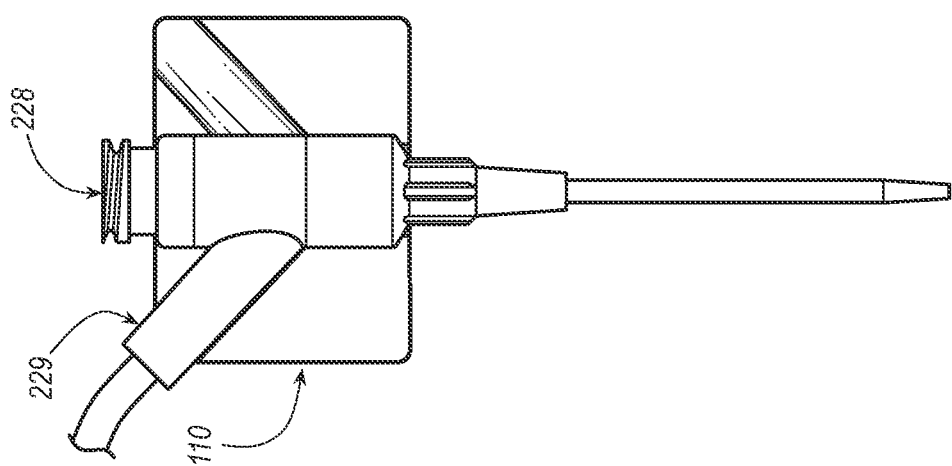
FIG. 4A illustrates the platform of the stabilization device with an extension port of an integrated catheter in a starboard-side recess of the platform in accordance with some embodiments.

The contoured recess 116 of the platform 110 is symmetrical for securing the extension port of an integrated catheter or an extension tube extending therefrom on either the starboard side of the platform 110 or the port side of the platform 110 by mere rotation of the integrated catheter along its central axis. See FIGS. 4A and 4B, which respectively illustrate the platform 110 of the stabilization device 100 with an extension port of an integrated catheter in the starboard-side recess 116b of the platform 110 and the port-side recess 116c of the platform 110 in accordance with some embodiments. The symmetrical contoured recess 116 provides orientation options to a clinician when stabilizing an integrated catheter, which include consideration of patient comfort as well.

Figure 5:
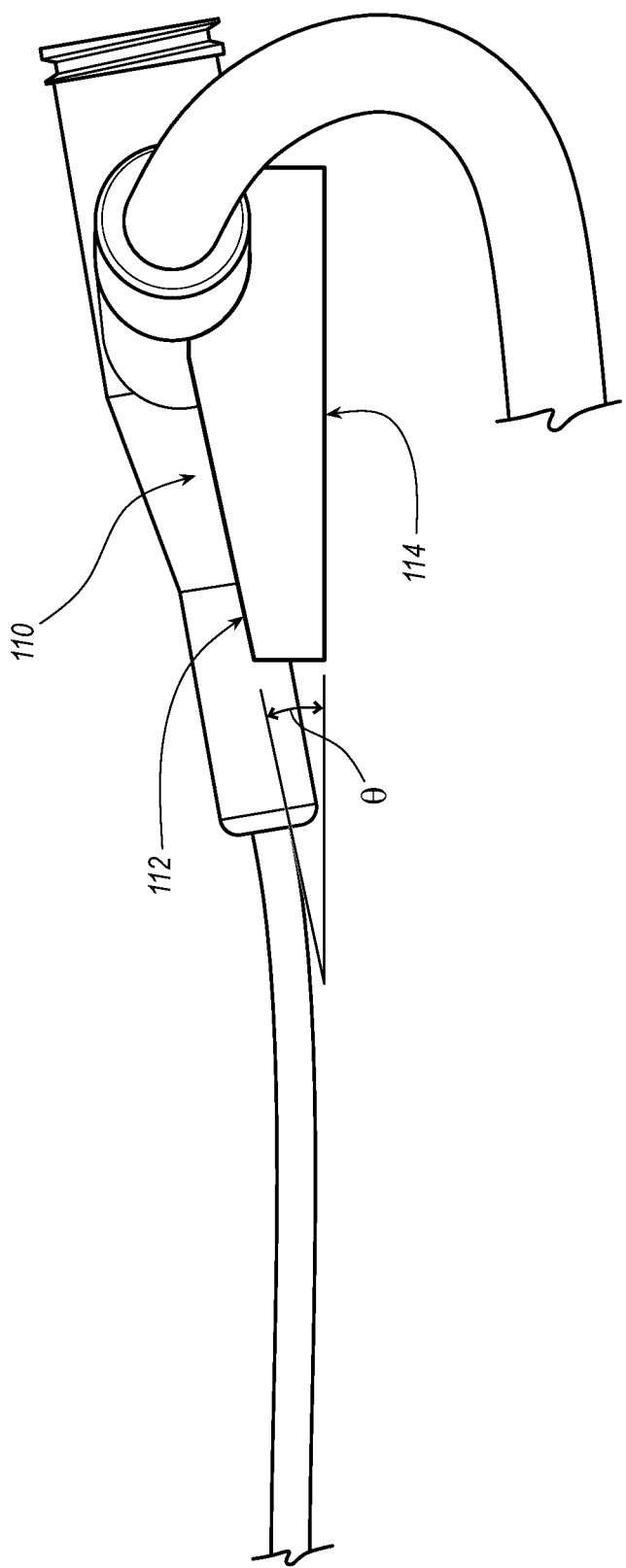
FIG. 5 illustrates a skin-adhering side and a catheter-securing side of the platform oblique to each other in accordance with some embodiments.

FIG. 5 illustrates the skin-adhering side 114 and the catheter-securing side 112 of the platform 110 oblique to each other in accordance with some embodiments.

While the skin-adhering side 114 and the catheter-securing side 112 of the platform 110 are parallel to each other from the front-end portion of the platform 110 to the back-end portion of the platform 110 in some embodiments, the skin-adhering side 114 and the catheter-securing side 112 of the platform 110 are oblique to each other in other embodiments. As shown in FIG. 5, the skin-adhering side 114 and the catheter-securing side 112 of the platform 110 can be oblique to each other with an angle θ. The angle θ can range from about 0, when the skin-adhering side 114 and the catheter-securing side 112 are parallel to each other, to about 45°. The angle θ, when less than about 30°, including less than about 15°, such as, less than about 10° (e.g., 8.5°) maintains an appropriate insertion angle for an integrated catheter while minimizing risk of kinking the catheter tube thereof. In addition, such an angle θ minimizes pistoning (e.g., back-and-forth movement within a blood vessel) at the insertion site.

Figure 6A:
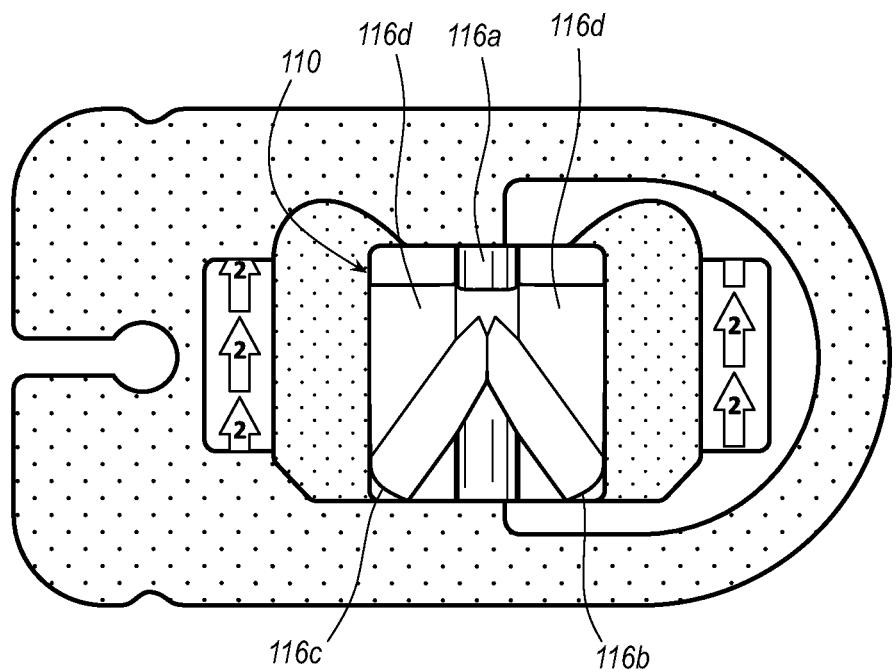
FIG. 6A illustrates the platform of the stabilization device with a wing-assembly recess of the platform in accordance with some embodiments.
Figure 6B:
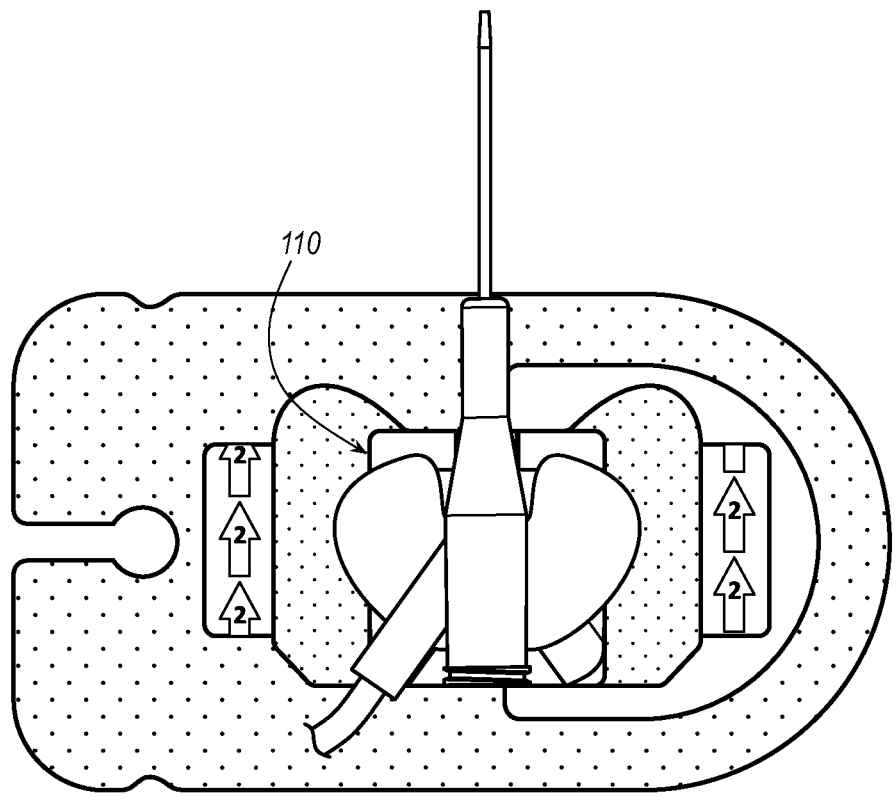
FIG. 6B illustrates the platform of the stabilization device with a wing assembly of an integrated catheter in the wing-assembly recess of the platform in accordance with some embodiments.

FIG. 6A illustrates the platform 110 of the stabilization device 100 with a wing-assembly recess 116*d* of the platform 100 in accordance with some embodiments, while FIG. 6B illustrates a wing assembly of an integrated catheter in the wing-assembly recess of the platform in accordance with some embodiments.

As set forth herein, the contoured recess 116 is configured to secure a catheter tube or a hub of an integrated catheter having an extension port angled with respect to the hub, a wing assembly, or both the extension port and the wing assembly. In addition to the contoured-recess portion 116*a* for the catheter tube or the hub of an integrated catheter and the contoured-recess portions 116*b* and 116*c* the extension port of an integrated catheter or an extension tube extending therefrom, the contoured recess 116 can include contoured-recess portion 116*d*. Contoured-recess portion 116*d* is configured to secure the wing assembly of an integrated catheter with a wing assembly. Because the wing assembly of integrated catheters with wing assemblies are typically symmetrical, the contoured-recess portion 116*d* is also symmetrical. Thus, the contoured recess 116 including the contoured-recess portion 116*d* can remain symmetrical providing the foregoing orientation options to a clinician when stabilizing an integrated catheter, which include consideration of patient comfort as well. In other embodiments, the contoured recess 116 including the contoured-recess portion 116*d* can be asymmetric providing a specific orientation option to a clinician when stabilizing an integrated catheter.

Figure 7A:
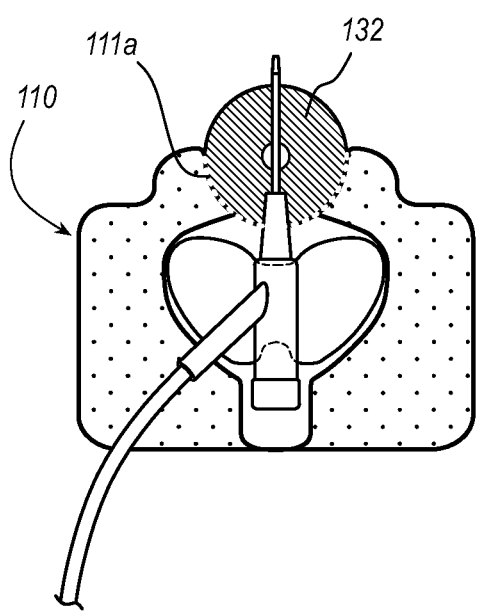
FIG. 7A illustrates a first cutout in the platform of the stabilization device for accessing a percutaneous insertion site in accordance with some embodiments.
Figure 7B:
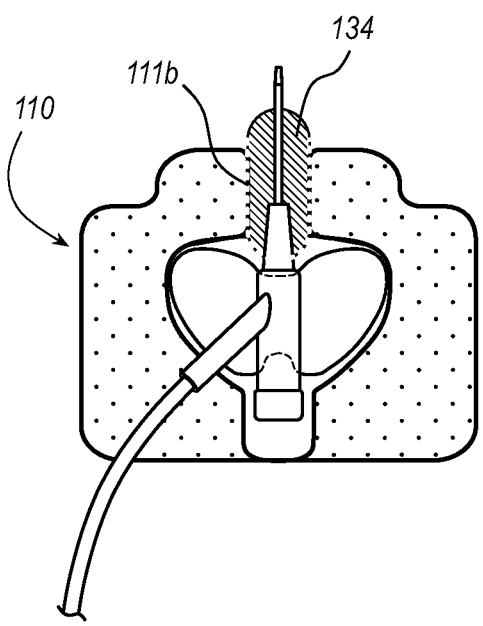
FIG. 7B illustrates a second cutout in the platform of the stabilization device for accessing a percutaneous insertion site in accordance with some embodiments.
Figure 7C:
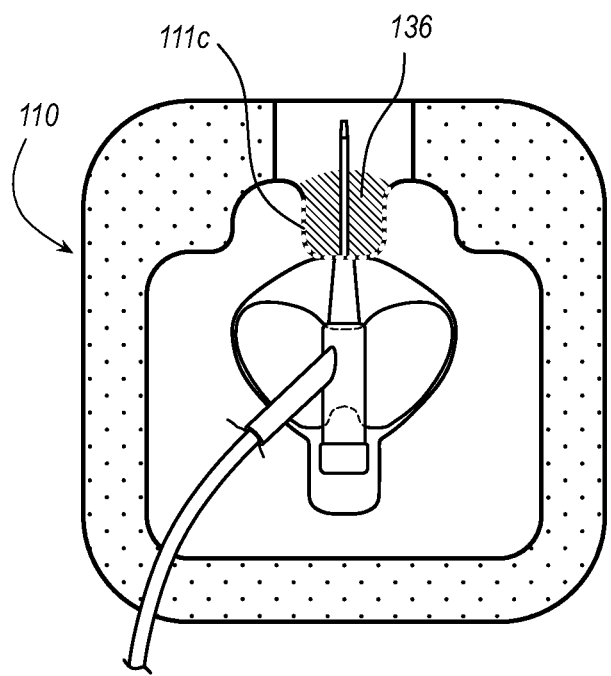
FIG. 7C illustrates a first cutout in the platform of the stabilization device for accessing a percutaneous insertion site in accordance with some embodiments.

FIGS. 7A, 7B, and 7C illustrate different cutouts 111 in the platform 110 of the stabilization device 100 for accessing a percutaneous insertion site in accordance with some embodiments.

As shown, the front-end portion of the platform 110 in each figure of FIGS. 7A, 7B, and 7C respectively includes a different cutout 111*a*, 111*b*, or 111*c* extending through the skin-adhering side 114 of the platform 110, each of which is configured for accessing a percutaneous insertion site through the platform 110 or near the front of platform 110. A stabilization system including the stabilization device 100 can further include antimicrobial pad 132 (e.g., BIOPATCH®, GuardIVa®) configured for placement within the cutout 111*a* and, thus, around the insertion site as shown in FIG. 7A for keeping the insertion site free of infection. The antimicrobial pad 132 is optionally integrated into the body on the skin-adhering side 114 of the platform 110. The stabilization system can further include a topical medicament 134 including an antimicrobial agent configured for application within the cutout 111*b* and, thus, around the insertion site as shown in FIG. 7B for keeping the insertion site free of infection. The cutout 111*b* localizes or contains the topical medicament 134, thereby keeping it at the insertion site. The stabilization system can further include a skin adhesive 136 configured for application within the cutout 111*c* and, thus, around the insertion site as shown in FIG. 7C for sealing the insertion site. The cutout 111*c* localizes or contains the skin adhesive 136, thereby keeping it at the insertion site. The skin adhesive 136 optionally includes a same or different antimicrobial agent than the topical medicament 134.

As shown in FIG. 1, the dressing 120 is configured to cover the platform 110 together with an integrated catheter secured in the platform 110 over a portion of a patient's skin at the stabilization site. The dressing includes a skin-adhering side configured to adhere the dressing 130 to both an integrated catheter secured in the platform 110 and the patient's skin.

The dressing 120 includes a transparent polymeric film 122 over a textile pad 124. The textile pad 124 has a cutout configured to form a window 126 for viewing a distal end of a catheter tube of an integrated catheter when the catheter tube is at or in the insertion site and the dressing covers the platform together with the integrated catheter secured in the platform at the stabilization site. The textile pad 124 forms a reinforced border around the window 126. While the textile pad 124 can have an additional cutout configured to form an additional window 128 for viewing a hub of an integrated catheter in the platform 110, such an additional window is not a necessity for an integrated catheter like it is for a non-integrated catheter. This is because an integrated catheter is manufacturer assembled to already include a reliable connection between the hub and extension tube of the integrated catheter, so the foregoing connection does not need to be monitored like it does in a non-integrated catheter. That said, the additional window 128 can be useful to a clinician for confirming an integrated catheter is present under the dressing 120.

The dressing 120 includes an opening 129 such as a through hole or a slit in the starboard side of the dressing 120, the opposite, port-side of the dressing 120, or both sides of the dressing 120 configured for an extension port or an extension tube of an integrated catheter to pass therethrough. Without the opening 129, the extension port or the extension tube of such an integrated catheter causes a gap between the dressing 120 and the patient's skin, which can allow microbes to enter the insertion site therethrough. Whether the opening 129 is a through hole or a slit, the dressing 120 is configured to securely wrap around an integrated catheter for both stability and decreased microbial ingress risk. When the opening 129 in the dressing 120 is a slit, the slit can have an angle matching that of the contoured recess 116 in the platform 110 when the contoured recess 116 is configured to secure an extension port of an integrated catheter. The angle can range from about 10° to about 170° (e.g., about 45°) from a longitudinal center line through the dressing.

A length of the dressing 120 from front to back is less than that needed for a dressing for existing stabilization devices for non-integrated catheters. This is because integrated catheters are not typically configured for additional connections in their proximal ends like non-integrated catheters. Integrated catheters already incorporate angled extension ports and extension tubes extending therefrom, which reduces axial footprints of different integrated catheters.

Figure 8:
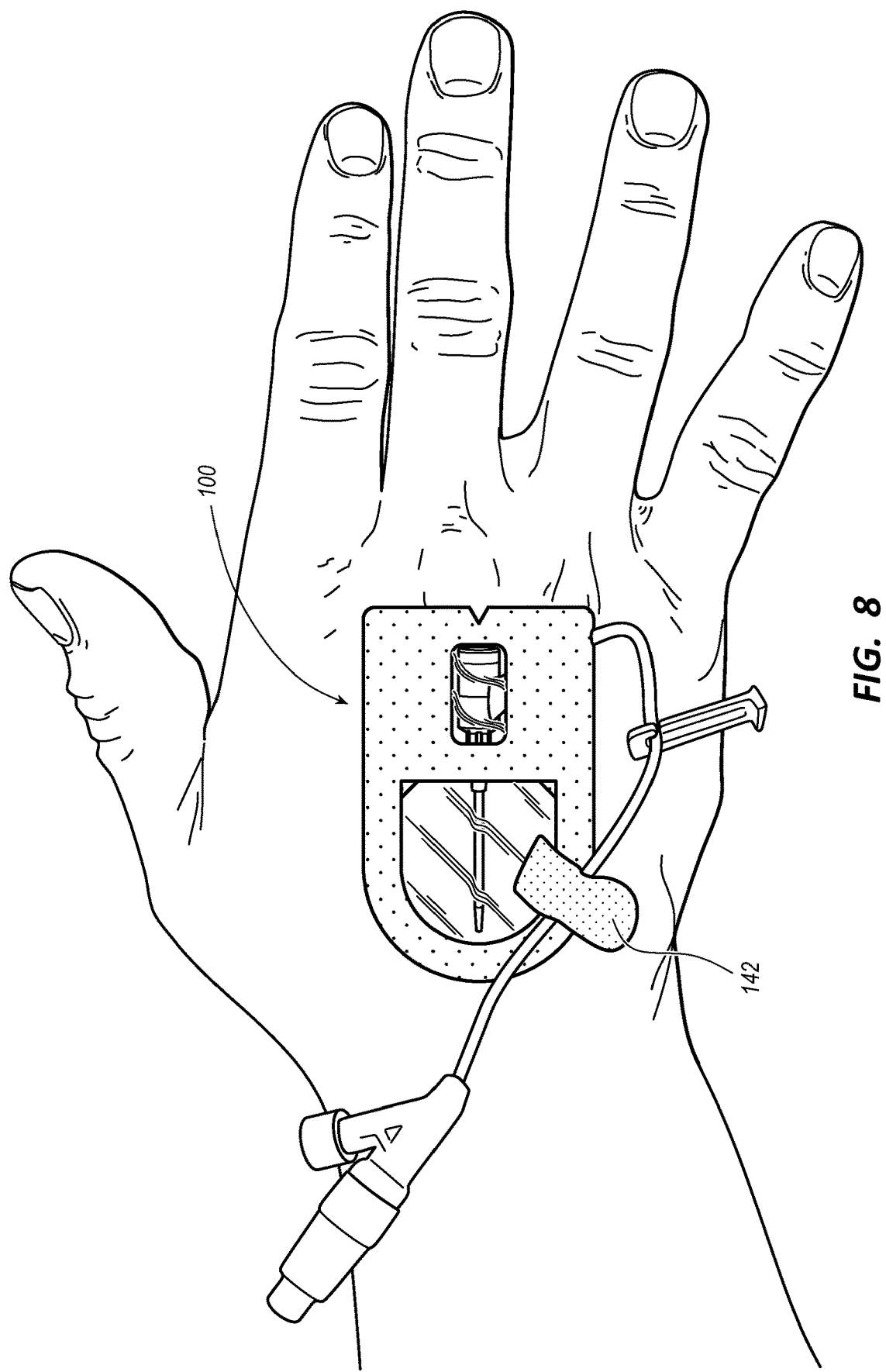
FIG. 8 illustrates a stabilization system securing an integrated catheter at a stabilization site of a patient with additional securement about an extension tube of the integrated catheter in accordance with some embodiments.

FIG. 8 illustrates a stabilization system including a stabilization device 100 securing an integrated catheter at a stabilization site of a patient with additional securement 142 about an extension tube of the integrated catheter in accordance with some embodiments. As shown, the additional securement 142 can include as a piece of tape configured for securement of an extension tube of an integrated catheter about the stabilization site.

A stabilization system including the stabilization device 100 (i.e., both the platform 110 and the dressing 120), instructions for use of the stabilization device 100, and any one or more additional components selected from the antimicrobial pad 132 (e.g., BIOPATCH®, GuardIVa®), the topical medicament 134, the skin adhesive 136, the additional securement 142, a degreasing wipe, and an antimicrobial wipe can be packaged as a ready-to-use stabilization kit.

A method for stabilizing integrated catheters includes removing a first adhesive backing from the catheter-securing side 112 of the platform 110 of the stabilization device 100 to expose the contoured recess 116 extending into the body of the platform 110; securing an integrated catheter in the contoured recess 116 by adhering it thereto, the integrated catheter including a catheter tube, a hub, and an extension port, a wing assembly, or both the extension port and the wing assembly; removing a second adhesive backing from the skin-adhering side 114 of the platform 110; adhering the platform 110 to a stabilization site on a patient's skin near a percutaneous insertion site; removing a third adhesive backing from the skin-adhering side of the dressing 120 of the stabilization device 120; and adhering the dressing 120 to the integrated catheter, the platform 110, and the patient's skin, thereby stabilizing the integrated catheter, decreasing risk of mechanical phlebitis, and increasing dwell time for the integrated catheter.

The method can further include accessing the insertion site in one or more ways of accessing the insertion site. Accessing the insertion site includes passing the catheter tube of the integrated catheter through any one of the cutouts 111a, 111b, or 111c and into the insertion site. Accessing the insertion site includes placing the antimicrobial pad 132 (e.g., BIOPATCH®, GuardIVa®) around the insertion site to keep the insertion site free of infection as shown in FIG. 7A. Accessing the insertion site includes applying the topical medicament 134 including an antimicrobial agent around the insertion site or sealing the insertion site with the skin adhesive 136 optionally including the same or different antimicrobial agent as shown in FIGS. 7B and 7C. When accessing the insertion site with the topical medicament 134, the cutout 111b localizes or contains the topical medicament 134, thereby keeping it at the insertion site. Likewise, when accessing the insertion site with the skin adhesive 136, the cutout 111c localizes or contains the skin adhesive 136, thereby keeping it at the insertion site. Not only does sealing the insertion site with the skin adhesive 136 prevent microbes from entering the insertion site, but sealing the insertion site has the added effect of further stabilizing an integrated catheter to a patient, thereby decreasing mechanical phlebitis.

The method can further include viewing a distal end of the catheter tube at the insertion site through the window 126 of the dressing 120 formed by the transparent polymeric film 122 over the cutout in the textile pad 124.

The method can further include inserting the extension port or the extension tube of the integrated catheter through the opening 129 (e.g., a through hole or a slit) in at least the starboard side of the dressing or the opposite, port-side of the dressing configured and taping the extension tube with the additional securement 142 (e.g., a piece of tape) about the stabilization site to further secure the integrated catheter.

The method can further include degreasing the patient's skin at the stabilization site with a degreasing wipe before adhering the platform 110 to the patient's skin.

The method can further include disinfecting the patient's skin at the stabilization site with an antimicrobial wipe before adhering the platform 110 to the patient's skin.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A stabilization system for an integrated catheter, comprising:
a platform having a thickness from a skin-adhering side to a catheter-securing side, wherein the platform is a foam-like material, wherein the skin-adhering side of the platform has a first adhesive thereon configured to adhere to a patient's skin, and wherein the catheter-securing side of the platform has a second adhesive thereon configured to adhere to the integrated catheter, the catheter-securing side of the platform including a contoured recess extending into the platform a distance less than the thickness, the contoured recess comprising:
a central channel along a longitudinal axis of the platform;
a first angled channel diverging from a first side of the central channel; and
a second angled channel diverging from a second side of the central channel, the second angled channel symmetrical with the first angled channel; and
a dressing configured to cover the platform together with the integrated catheter secured in the platform over the patient's skin.

2. The stabilization system according to claim 1, wherein the skin-adhering side and a non-recessed catheter-securing side of the platform are parallel to each other from a catheter tube-securing front-end portion of the platform to an opposite, back-end portion of the platform.

3. The stabilization system according to claim 1, wherein the skin-adhering side and a non-recessed catheter-securing side of the platform are oblique to each other from a catheter tube-securing front-end portion of the platform to an opposite, back-end portion of the platform.

4. The stabilization system according to claim 1, further comprising an antimicrobial pad configured for placement around an insertion site, wherein the antimicrobial pad is integrated into the skin-adhering side of the platform.

5. The stabilization system according to claim 1, wherein the dressing includes a transparent polymeric film over a textile pad, the textile pad having a cutout configured to form a window for viewing a distal end of a catheter tube of the integrated catheter when the dressing covers the platform together with the integrated catheter secured in the platform over the patient's skin.

6. The stabilization system according to claim 1, wherein the skin-adhering side is configured to adhere the dressing to both the integrated catheter secured in the platform and the patient's skin.

7. The stabilization system according to claim 1, wherein the dressing includes a through hole or slit in at least a starboard side of the dressing or an opposite, port-side of the dressing configured for an extension port or an extension tube of the integrated catheter to pass therethrough.

8. The stabilization system according to claim 1, further comprising a topical medicament including an antimicrobial agent configured for application around an insertion site, and a skin adhesive configured for sealing the insertion site, wherein the skin adhesive includes the antimicrobial agent in the topical medicament.

9. A stabilization system for an integrated catheter, comprising:
a platform having a thickness from a skin-adhering side to a catheter-securing side, wherein the platform is a foam-like material, wherein the skin-adhering side of the platform has a first adhesive thereon configured to adhere to a patient's skin, and wherein the catheter-securing side of the platform has a second adhesive thereon configured to adhere to the integrated catheter, the catheter-securing side of the platform including a contoured recess extending into the platform a distance less than the thickness, the contoured recess comprising:
- a central channel along a longitudinal axis of the platform;
- a first angled channel diverging from a first side of the central channel; and
- a second angled channel diverging from a second side of the central channel, the second angled channel symmetrical with the first angled channel; and a dressing including a transparent polymeric film over a textile pad, the dressing having the skin-adhering side configured to adhere the dressing to both the integrated catheter secured in the platform and the patient's skin.

10. The stabilization system according to claim 9, wherein the skin-adhering side and a non-recessed catheter-securing side of the platform are oblique to each other from a catheter tube-securing front-end portion of the platform to an opposite, back-end portion of the platform.

11. The stabilization system according to claim 9, wherein the textile pad has a cutout configured to form a window for viewing a distal end of a catheter tube of the integrated catheter when the dressing covers the platform together with the integrated catheter secured in the platform over the patient's skin.

12. The stabilization system according to claim 9, wherein the dressing includes a through hole or slit in at least a starboard side of the dressing or an opposite, port-side of the dressing configured for an extension port or an extension tube of the integrated catheter to pass therethrough.

13. The stabilization system according to claim 9, further comprising an antimicrobial pad configured for placement around a percutaneous insertion site, wherein the antimicrobial pad is integrated into the skin-adhering side of the platform.

14. A method for stabilizing integrated catheters, comprising:

removing a first adhesive backing from a catheter-securing side of a platform of a stabilization device to expose a contoured recess extending into the platform a distance less than a full thickness of the platform, wherein the platform is a foam-like material, the contoured recess comprising:
- a central channel along a longitudinal axis of the platform;
- a first angled channel diverging from a first side of the central channel; and
- a second angled channel diverging from a second side of the central channel, the second angled channel symmetrical with the first angled channel;

securing an integrated catheter in the contoured recess by adhering it thereto, the integrated catheter including a central portion received in the central channel of the contoured recess and a side portion received in one of the first angled channel and the second angled channel;

removing a second adhesive backing from a skin-adhering side of the platform;

adhering the platform to a stabilization site on a patient's skin near a percutaneous insertion site;

removing a third adhesive backing from a skin-adhering side of a dressing of the stabilization device; and adhering the dressing to the integrated catheter, the platform, and the patient's skin, thereby stabilizing the integrated catheter and decreasing risk of mechanical phlebitis.

15. The method according to claim 14, further comprising viewing a distal end of the integrated catheter at the percutaneous insertion site through a window of the dressing formed by a transparent polymeric film over a cutout in a textile pad.

16. The method according to claim 14, further comprising inserting an extension port or an extension tube of the integrated catheter through a through hole or slit in at least a starboard side of the dressing or an opposite, port-side of the dressing and taping the extension tube about the stabilization site to further secure the integrated catheter.

* * * * *